United States Patent [19]
Carroll et al.

[11] Patent Number: 5,932,751
[45] Date of Patent: Aug. 3, 1999

[54] EPOXIDATION CATALYST AND PROCESS

[75] Inventors: Kevin M. Carroll, Havertown; Yuan-Zhang Han; Edrick Morales, both of West Chester, all of Pa.

[73] Assignee: ARCO Chemical Technology, L.P., Greenville, Del.

[21] Appl. No.: 09/103,257

[22] Filed: Jun. 23, 1998

[51] Int. Cl.⁶ .................................................. C07D 301/19
[52] U.S. Cl. ............................................................ 549/529
[58] Field of Search ............................................. 549/529

[56] References Cited

U.S. PATENT DOCUMENTS

| | | | |
|---|---|---|---|
| 3,351,635 | 11/1967 | Kollar | 260/348.5 |
| 3,829,392 | 8/1974 | Wulff | 252/430 |
| 3,923,843 | 12/1975 | Wulff | 260/348.5 |
| 4,021,454 | 5/1977 | Wulff et al. | 260/348.5 L |
| 4,367,342 | 1/1983 | Wulff et al. | 549/529 |

FOREIGN PATENT DOCUMENTS 1249079  10/1971  United Kingdom .

OTHER PUBLICATIONS

"Influence of the preparation method of the $V_2O_5/TiO_2/SiO_2$ catalysts in selective reduction of nitric oxide with ammonia", Wauthog et al. Applied Catalysis 69, pp. 149–167 (1991).

*Primary Examiner*—Amelia Owens
*Attorney, Agent, or Firm*—William C. Long

[57] ABSTRACT

A titanium/silica epoxidation catalyst is prepared from silica which has been treated with strong aqueous acid solution, the catalyst is especially useful for propylene oxide production.

6 Claims, No Drawings

EPOXIDATION CATALYST AND PROCESS

BACKGROUND OF THE INVENTION

1. Field of the Invention

The present invention relates to the preparation of a titanium on silica catalyst and to the use of the catalyst for the epoxidation of olefins to produce products such as propylene oxide.

2. Description of the Prior Art

A process for the epoxidation for olefins such as propylene to produce the oxirane product such as propylene oxide involves the reaction of the olefin with an organic hydroperoxide in the presence of various catalyst materials. The basic patent which describes this process is U.S. Pat. No. 3,351,635.

A particular embodiment of this technology which has been commercially practiced involves the use of a solid epoxidation catalyst comprised of titanium on silica. There are a number of patents which describe this embodiment of the technology including U.S. Pat. Nos. 3,829,392, 3,923,843, 4,021,454, 4,367,342, and British Patent 1,249,079.

Although good results have been achieved with the titanium on silica catalyzed epoxidation of olefins, there remains room for further improvement. It is an objective of the present invention to provide an improved epoxidation catalyst of the titania on silica type and to provide a process for the epoxidation of olefins using this catalyst.

In the technology associated with catalytic reduction of nitric oxide with ammonia the preparation of titania on silica catalysts has been described where the silica has been pretreated by refluxing in hydrochloric acid. See Applied Catalysis 69, p. 149–167 (1991), "Influence of the preparation method on the $V_2O_5/TiO_2/SiO_2$ catalysts in selective reduction of nitric oxide with ammonia", Wauthog et al.

BRIEF DESCRIPTION OF THE INVENTION

The present invention involves the preparation of an improved titanium on silica epoxidation catalyst and the use thereof in organic hydroperoxide epoxidations. Specifically, the invention involves acid washing the silica prior to the deposition of the titanium component thereon whereby improved catalyst epoxidation activity is obtained.

DETAILED DESCRIPTION

The general technology with which the present invention is associated is the, by now, well known reaction of an organic hydroperoxide with an olefin to produce the product oxirane compound. U.S. Pat. No. 3,351,635 provides a comprehensive description of the various olefin and hydroperoxide reactants which are involved in this reaction.

The titanium on silica catalysts are generally represented in their preparation and use by the plurality of patents described above. That is, practice of the invention is useful as an improvement in the context of the known reaction systems whereby an organic hydroperoxide and olefin are reacted using a solid titanium on silica catalyst.

The essence of the present invention resides in treating the silica catalyst component with an aqueous acid prior to the deposition of the titanium component thereon. The acid treatment is carried out using an aqueous solution of a strong acid; suitable acids are sulfuric acid, hydrochloric acid, phosphoric acid, nitric acid, acetic acid, and the like. In accordance with the present invention, an aqueous solution comprising the acid is prepared and particles of the silica, which with titanium, is to form the epoxidation catalyst are immersed in the acidic solution. Generally the silica particles are maintained in the acid solution at a temperature illustratively of 5–150° C. for a period of the order of 30 minutes to 200 hours. Alternatively, the soild catalyst particles can be packed in a fixed bed and the acid solution flowed through the bed. At the completion of this acid treatment, the solid silica particles are separated from the aqueous acid as by filtration and washed with de-ionized water to remove residual traces of acid treating material. Following this wash, which may be several successive washes, the treated silica particles can be washed one or more times with alcohol and are then ready for deposition thereon of the titania forming component.

In accordance with the invention, techniques previously used in the prior art are employed in order to deposit the titanium component on the acid treated silica particles. The various deposition procedures together with the preferred after-silylation of the treated catalyst as shown in U.S. Pat. Nos. 3,829,392, 3,923,843, 4,021,454, and 4,367,342 as well as UK 1,249,079 are conveniently employed in the preparation of the final catalyst composition. The disclosures of these references are incorporated herein by reference. The final catalyst composition comprises titanium in chemical combination with the acid treated silica.

The improved catalyst of the invention can be employed in the production of oxirane compounds by reaction of an olefin and an organic hydroperoxide in accordance with, procedures known in the art. A characteristic of the catalyst prepared in accordance with the invention when compared with a similar catalyst but one which has not had the silica acid treatment is that the catalyst of the invention demonstrates surprising and significantly improved activity in the epoxidation reaction.

As above described, the conditions and reactants which are employed in the epoxidation using the inventive catalyst are as described in the prior art. The invention is especially advantageously applied to the production of propylene oxide by reaction of propylene with an organic hydroperoxide such as tertiary butyl hydroperoxide or ethylbenzene hydroperoxide.

In order to further illustrate the invention, the following examples are provided.

EXAMPLES

Acid Washing of Silica Support

Silica (Grace V432, 30 g) is washed with HCl (0.4 M, 2500 cc) in a fixed bed reactor at 70° C. and 150 psi, the acid flow rate being 8.33 cc/min. The silica is then washed with deionized water (750 cc) to remove any residual chloride followed by an IPA (750 cc)wash. Catalyst is removed from the reactor and dried at 400° C. in a muffle furnace. The silica was tested before and after washing for metal impurities, and the results are shown in Table 1. The amount of each impurity, with the exception of Fe (possibly from stainless steel), is reduced.

TABLE 1

Impurity profile of washed and non-washed silica

| Silica Impurity | Amount before wash (ppm by weight of silica) | Amount after wash (ppm by weight of silica) |
|---|---|---|
| Na | 800 | 100 |
| Al | 250 | 100 |
| Ca | 120 | 42 |
| K | 50 | <20 |
| Mg | 20 | 12 |
| Fe | 40 | 87 |

Catalyst Preparation

The epoxidation catalyst is produced by the incipient wetness method. The acid washed silica (14.5 g) is weighed into a 250 cc round-bottomed flask. A mixture Ti(acac)$_2$ ($^i$OPr)$_2$(1.5 g) in anhydrous IPA (14.5 g) is added to the silica. The reaction mixture is thoroughly mixed for 0.5 hours then residual solvent is removed on a rotary evaporator. The catalyst is then calcined in a muffle furnace at 800° C. and then silylated at 200° C. with hexamethyldisilazane (2.5 cc) for 3 hours in a quartz tube heated in a 3-zone furnace.

A similar catalyst was prepared by the same method using non-acid washed silica as a comparative example.

Batch Epoxidation of 1-Octene with EBHP Oxidate

Catalyst (0.5 g) was added to a 4-neck round-bottomed flask charged with a condenser, a thermocouple, a stir bar and a sampling port. A mixture containing 17.0 g 1-octene, 10 g EBHP oxidate and 1 g nonane (internal standard) was added to the flask. A sample was taken after the reaction mixture was stirred thoroughly under inert atmosphere. The mixture was heated to 90° C. and the reaction lasted for 1 hour at 90° C.

The batch epoxidation results obtained for the catalysts are shown in Table 2. The catalyst prepared using acid washed silica in accordance with the invention was more active by 11% conversion points than that prepared using non-acid washed silica.

TABLE 2

Batch Epoxidation Results of 1-Octene with EBHP Oxidate

| Catalyst from | % Ti | % C | Conversion (%) | Selectivity (%) |
|---|---|---|---|---|
| Acid washed silica | .89 | 2.3 | 80 | 82 |
| Non-washed comparison | .94 | 1.81 | 69 | 89 |

We claim:

1. A process for the preparation of an oxirane compound which comprises reacting an olefinic compound with an organic hydroperoxide in the presence of a titanium on silica catalyst, said silica having been treated with aqueous acid.

2. The process of claim 1 wherein the aqueous acid is aqueous HCl.

3. The process of claim 1 wherein the olefinic compound is propylene.

4. The process of claim 1 wherein the organic hydroperoxide is ethylbenzene hydroperoxide.

5. The process of claim 1 wherein the organic hydroperoxide is tertiary butyl hydroperoxide.

6. The process of claim 1 wherein the catalyst is silylated.

* * * * *